(12) United States Patent
Neff

(10) Patent No.: US 7,175,626 B2
(45) Date of Patent: Feb. 13, 2007

(54) DYNAMIC COMPRESSION DEVICE AND DRIVING TOOL

(75) Inventor: James R. Neff, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 10/868,087

(22) Filed: Jun. 15, 2004

(65) Prior Publication Data

US 2005/0277940 A1 Dec. 15, 2005

(51) Int. Cl.
*A61B 17/56* (2006.01)
*A61F 2/30* (2006.01)

(52) U.S. Cl. .................................................. 606/73

(58) Field of Classification Search ................ 606/53, 606/60, 86, 72, 73, 104; 411/383, 384, 392
See application file for complete search history.

(56) References Cited

U.S. PATENT DOCUMENTS

| | | | |
|---|---|---|---|
| 4,249,444 A | | 2/1981 | Lee |
| 4,432,358 A | * | 2/1984 | Fixel .......................... 606/66 |
| 4,947,502 A | | 8/1990 | Engelhardt |
| 4,959,064 A | | 9/1990 | Engelhardt |
| 5,047,030 A | | 9/1991 | Draenert |
| 5,057,111 A | * | 10/1991 | Park ........................... 606/69 |
| 5,061,137 A | * | 10/1991 | Gourd ......................... 411/510 |
| 5,102,276 A | * | 4/1992 | Gourd ......................... 411/392 |
| 5,702,398 A | * | 12/1997 | Tarabishy .................... 606/72 |
| 5,791,850 A | * | 8/1998 | Mundt et al. ................ 411/508 |
| 5,797,912 A | * | 8/1998 | Runciman et al. ........... 606/69 |
| 6,197,065 B1 | * | 3/2001 | Martin et al. ............ 623/23.17 |
| 6,283,969 B1 | | 9/2001 | Grusin et al. |
| 6,315,779 B1 | | 11/2001 | Morrison et al. |
| 6,322,562 B1 | * | 11/2001 | Wolter ........................ 606/69 |
| 6,331,179 B1 | | 12/2001 | Freid et al. |
| 6,428,542 B1 | | 8/2002 | Michelson |
| 6,436,100 B1 | | 8/2002 | Berger |
| 6,443,954 B1 | | 9/2002 | Bramlet et al. |
| 6,458,134 B1 | | 10/2002 | Songer et al. |
| 6,475,242 B1 | | 11/2002 | Bramlet |
| 6,517,543 B1 | | 2/2003 | Berrevoets et al. |
| 6,558,423 B1 | | 5/2003 | Michelson |
| 6,656,184 B1 | | 12/2003 | White et al. |
| 2001/0007074 A1 | * | 7/2001 | Strobel et al. ................ 606/73 |
| 2001/0047174 A1 | | 11/2001 | Donno et al. |
| 2002/0099386 A1 | | 7/2002 | Beger et al. |

FOREIGN PATENT DOCUMENTS

EP 0767631 B1 12/2000

OTHER PUBLICATIONS

*Managing Motion, Utilizing Heli-Cal Flexure Technology*, by Helical Products Company, Inc., pp. 1-32.

* cited by examiner

*Primary Examiner*—Eduardo C. Robert
*Assistant Examiner*—Anuradha Ramana
(74) *Attorney, Agent, or Firm*—Bracewell & Giuliani LLP

(57) ABSTRACT

A bone screw has a spring section to allow the screw to elongate while it is being installed. The screw has a cavity with a proximal drive surface and a distal drive surface. The drive surfaces are located on opposite sides of the spring section. A drive tool that has proximal and distal drive members fits within the cavity. Rotating the drive tool transmits torque to both the proximal and distal drive sockets simultaneously.

18 Claims, 4 Drawing Sheets

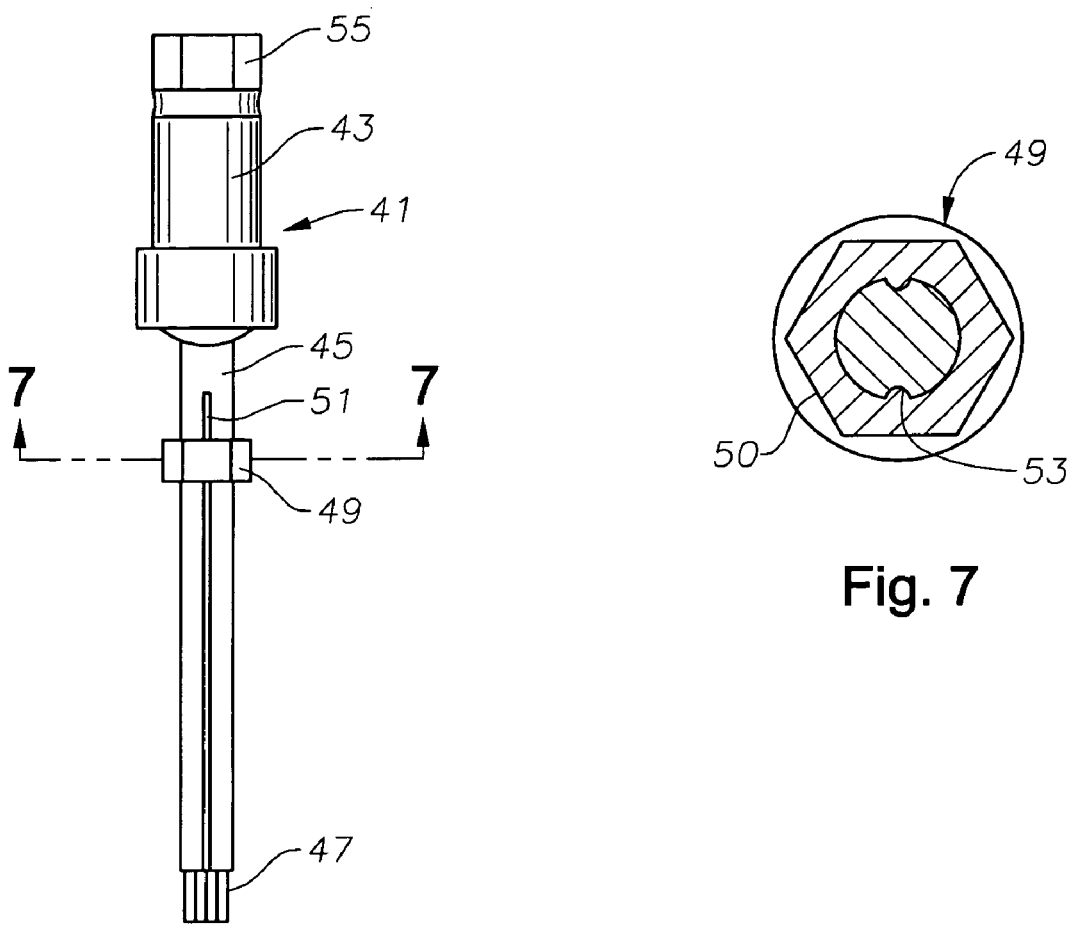
Fig. 4
Fig. 7
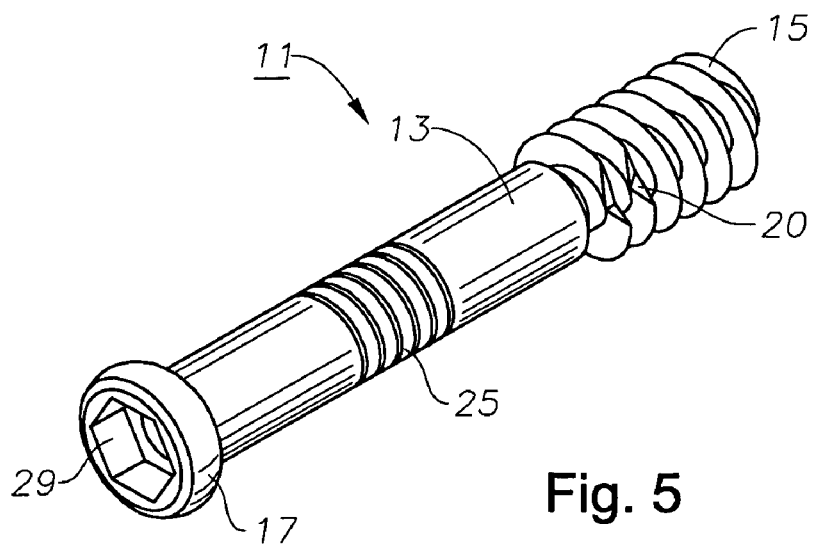
Fig. 5

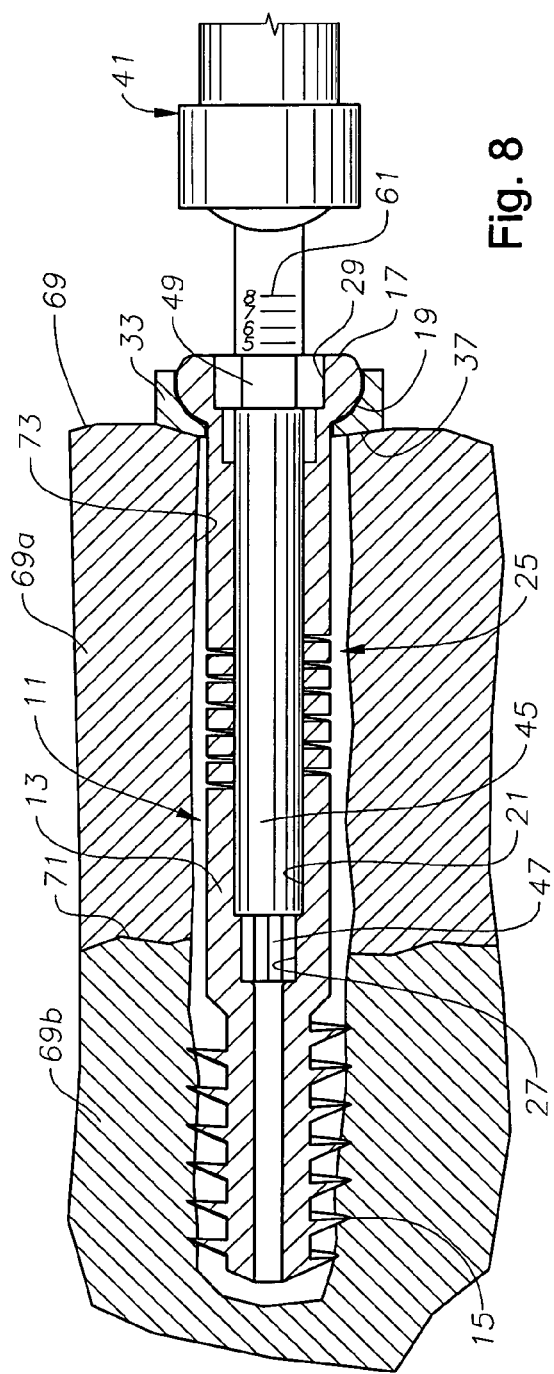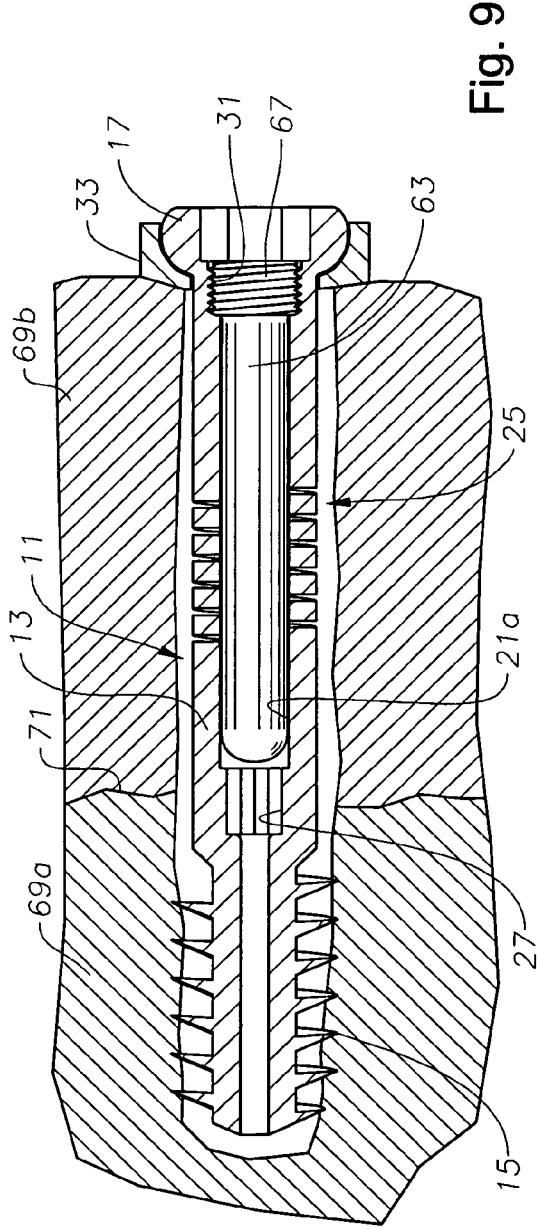

us 7,175,626 B2

DYNAMIC COMPRESSION DEVICE AND DRIVING TOOL

FIELD OF THE INVENTION

This invention relates in general to fasteners for fastening portions of a fractured bone together.

BACKGROUND OF THE INVENTION

One method of bone fracture repair comprises securing screws across the fractured portions of the bone. The purpose of the screw or screws is to tightly secure the bone fragments together while the bone heals. Typically, the screws comprise lag design, each being a solid member having an externally threaded section on one end and a head on the other end. The head bears against the exterior surface of the bone when the screw is secured to a desired torque to place the bone fragments in compression.

During the process of revascularization, the edges of the fracture commonly will resorb, typically about 1 to 3 mm. This movement reduces or eliminates the initial compression that the screw has provided. A bone lag screw that could provide continuous dynamic compression across the fracture while accommodating resorption as the bone heals would provide improved long-term stabilization until revascularization is completed.

A number of patents disclose a spring section within a lag screw for this purpose. The spring section would allow the screw to elongate slightly as it is being inserted. If sufficient initial compression existed, the spring section would provide dynamic compression during the repair process. The spring sections shown in these patents, however, could be damaged during insertion because the torque applied to the head of the screw passes through the spring section. This torque would result in torsional deformation of the spring section during insertion, which could create stress risers within the spring that could lead to early mechanical failure. Furthermore, during the process of removal, the spring could distort and fail mechanically, requiring extraction methods that could be more destructive to the bone.

SUMMARY OF THE INVENTION

In this invention, the dynamic compression device in the preferred embodiment is a screw having an elongated body with a distal end and a proximal end. The device has an external anchor section and a spring section located between the ends. A proximal drive surface is located proximal of the spring section. A distal drive surface is at a location distal of the spring section.

A drive tool is employed that has two spaced-apart drive members. One of the drive members engages the distal drive surface while the other drive member engages the proximal drive surface. These two drive members apply torque simultaneously to the screw body on opposite ends of the spring section to assure that the spring section does not undergo torsion during deployment.

In the preferred embodiment, the screw is hollow, and the distal drive surface comprises a socket located within the cavity of the screw. The proximal drive surface is also preferably a drive socket, and it is located within a recess in the head. The tool has an elongated shank with the distal drive member located on the tip. The proximal drive member is slidably carried on the shank but rotates with the shank.

The screw of this invention has an enlarged head in the preferred embodiment, the head having a flange that is partially spherical. A washer fits between the flange and the bone surface, and has one side for engaging the bone exterior. The interior of the washer comprises a mating spherical surface for engaging the flange of the head. The spherical surface allows the axis of the washer to incline relative to the axis of the screw.

A stabilizing pin preferably fits within the cavity of the screw after the tool has been removed. The stabilizing pin extends through the spring section, reducing bending moments and protecting the spring. Also, the stabilizing pin retards bone ingrowth into the cavity. Reducing bone ingrowth makes the task of removing the screw easier if the screw is later removed.

BRIEF DESCRIPTION OF THE DRAWINGS

FIG. 4 is a side elevational view of a tool constructed in accordance with this invention for deploying the screw of FIG. 1.

FIG. 5 is a perspective view of the screw of FIG. 1.

FIG. 7 is a sectional view of the tool of FIG. 4, taken along the line 7—7 of FIG. 4.

FIG. 8 is a sectional view of the screw of FIG. 1 with the tool of FIG. 4 inserted.

FIG. 9 is a sectional view of the screw of FIG. 1 installed within a bone and containing the stabilizing pin of FIG. 1.

DETAILED DESCRIPTION OF THE INVENTION

Figure 1:
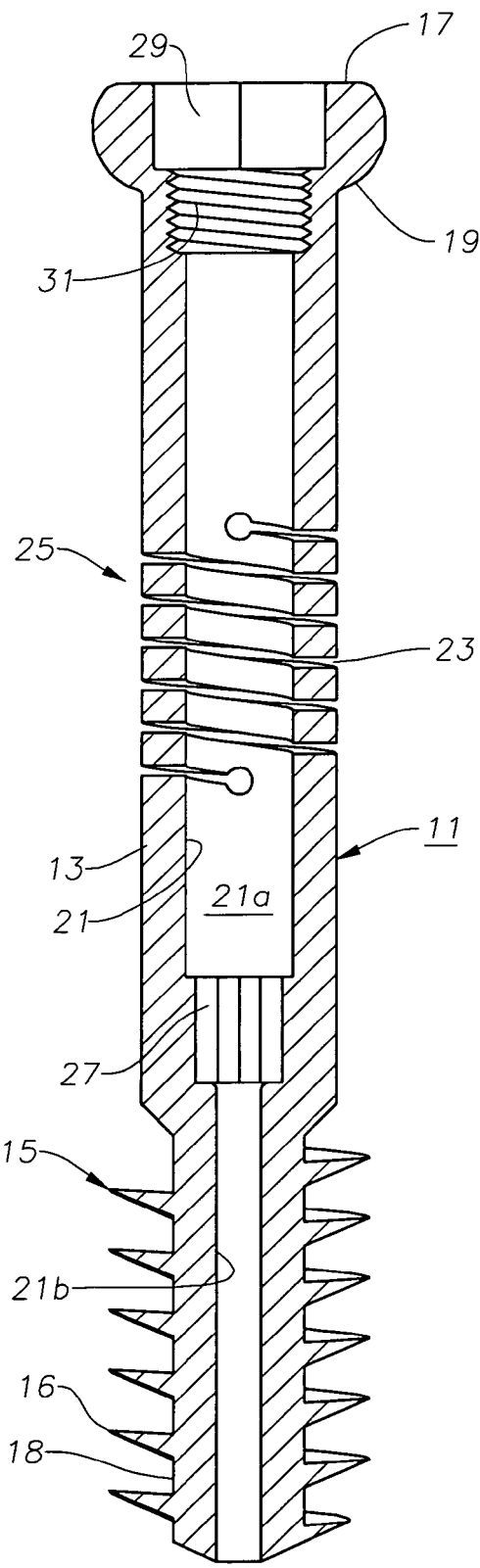
FIG. 1 is a sectional view of a screw constructed in accordance with this invention.

Referring to FIG. 1, the fastener of this invention includes comprises a screw 11 in the preferred embodiment that has an elongated body 13. Screw 11 may be formed of various biocompatible materials such as stainless steel or vitallium, but preferably is formed of titanium or titanium alloy because of the enhanced fatigue properties.

Screw body 13 has an anchor section on its distal end, which preferably comprises a set of external threads 15. Threads 15 may be a variety of types, but are shown as having a saw-tooth configuration with a sharp crest 16. A cylindrical root 18 locates between adjacent crests 16. The outer diameter of threads 15 measured at crests 16 is uniform, except for the first thread 15 at the distal end, which is slightly smaller. The outer diameter of threads 15 is larger than the outer diameter of body 13. Threads 16 have a low pitch, a considerable dimension from root 18 to crest 16, and resemble a flight of an auger. As shown in FIG. 5, one or two of the threads 15 at the proximal end may have back cut notches or flutes 20 formed in them to facilitate re-cutting a threaded profile in a bone if screw 11 is to be removed. Other types of anchor features are also feasible for anchoring body 13 to an object by rotation. For example, helical flight segments that do not extend fully circumferentially may be feasible in lieu of threads 15, particularly when the device is to be used other than as a bone screw.

As shown in FIG. 1, an enlarged head 17 is formed on the proximal end of body 13. Head 17 has a radially extending flange 19. The distal side of flange 19 is rounded, or partially spherical. A cavity 21 extends axially within body 13. Cavity 21 has a first portion 21a (FIG. 1) that is larger in diameter than the second portion 21b. Second portion 21b is located within threaded section 15. Cavity 21 extends completely through screw 11 from head 17 to the opposite end.

A helical slot 23 extends from the inner diameter of cavity portion 21a to the outer diameter of body 13, defining a helical rib that forms a spring section 25. In this embodiment, slot 23 is located in a proximal portion of body 13, beginning near head 17 and extending downward about half the length of cavity first portion 21a. However, slot 23 could be located at other points within body 13 between head 17 and threads 15. Spring section 25 will plastically deflect to allow axial elongation and compression of body 13.

A distal drive surface 27 is located between threaded section 15 and spring section 25. Distal drive surface 27 is preferably a drive socket having a plurality of drive surfaces or flanks located within cavity 21 at its junction with cavity second portion 21b. Body 13 also has a proximal drive surface 29 located proximally of spring section 25. Preferably, proximal drive surface 29 comprises a drive socket formed in head 17 and surrounded by flange 19. Alternately, proximal drive surface 29 could be formed on the outer diameter of flange 19. Distal and proximal drive sockets 27, 29 could be of a variety of shapes for causing rotation of screw 11, such as hex, splines or Torx. In the embodiment shown, distal drive socket 27 and proximal drive socket 29 are shown as hex sockets. Proximal drive socket 29 has a larger diameter than distal drive socket 27.

Figure 3:
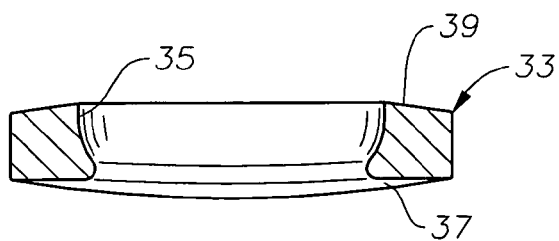
FIG. 3 is an enlarged view of a washer for use with the screw of FIG. 1.

An internally threaded section 31 is optionally located in cavity portion 21a between head 17 and spring section 25 for a purpose that will subsequently be explained. Referring to FIG. 3, a washer 33 is preferably employed with screw 11. Washer 33 is an annular member of biocompatible material having a hole 35 through it that is partially spherical. Hole 35 is concave, providing a smaller inner diameter at its distal side 37 than its proximal side 39. This results in a concave surface that is formed at the same contour as flange 19 for mating with flange 19. Distal side 37 may be slightly concave, as shown or of varying contours and textures.

Figure 6:
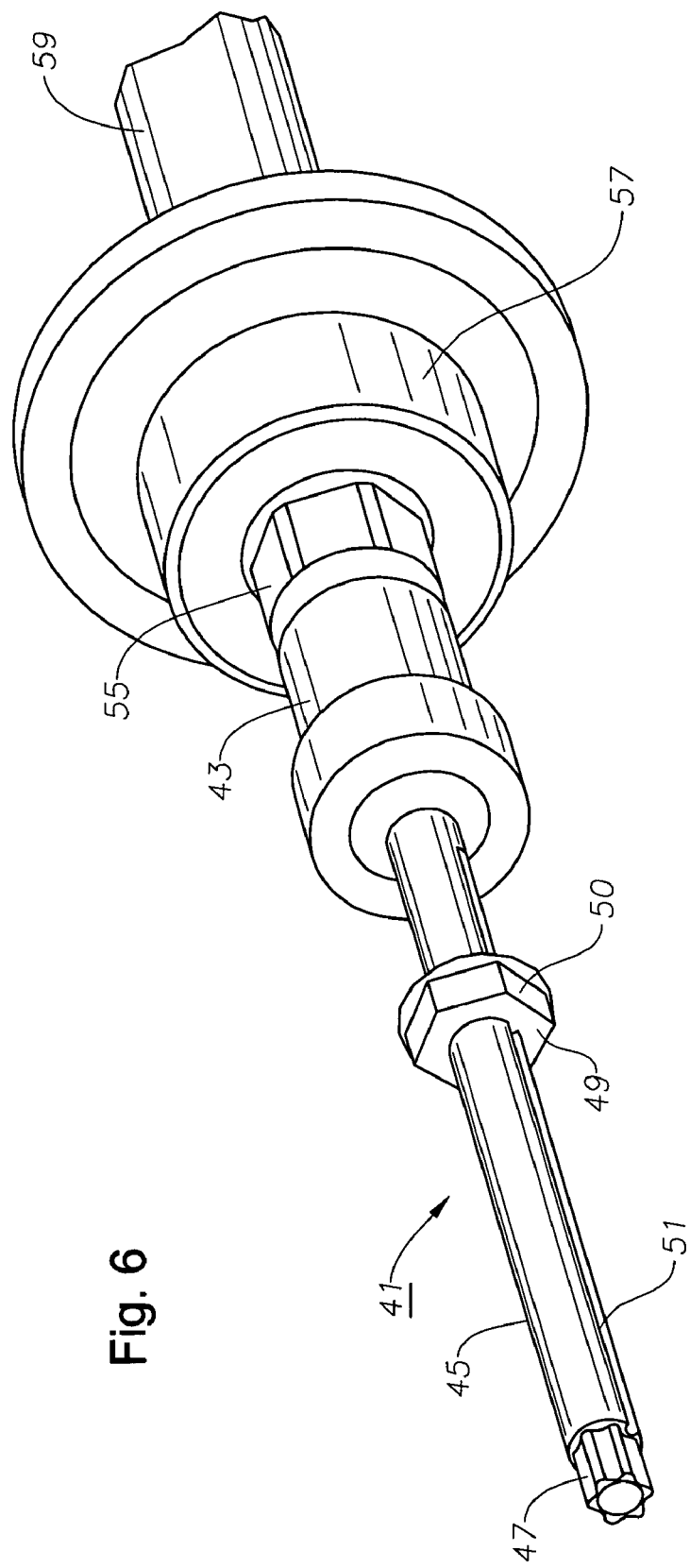
FIG. 6 is a perspective view of the tool of FIG. 4.

A tool 41, shown in FIGS. 4 and 6, is used to deploy screw 11 (FIG. 1). Tool 41 has a base 43 and a reduced diameter shank 45 extending from it. Shank 45 is a cylindrical member having a distal drive member 47 integrally formed on its distal end. Shank 45 could be other configurations rather than cylindrical, such as hexagonal. Drive member 47 has an exterior surface contoured to mate with distal drive socket 27. For illustration purposes, drive member 47 is shown as hexagonal in FIG. 4 and with a Torx configuration in FIG. 6.

Tool 41 also has a proximal drive member 49. Proximal drive member 49, as shown also in FIG. 7, is an annular member similar to a nut having drive flanks 50 on its exterior side that mate with proximal drive socket 29. In the embodiment shown, drive flanks 50 are hexagonal. If screw proximal drive surface 29 were alternately located on the exterior of head 17, proximal drive member 49 would be a sleeve having drive flanks in its interior. Shank 45 of tool 41 has at least one groove 51 that extends axially. A key 53 formed in the inner diameter of proximal drive 49 engages groove 51 to cause proximal drive member 49 to rotate with shank 45. In the preferred embodiment, there are two grooves 51 spaced 180 degrees apart from each other and two keys 53. Rather than key 53 and groove 51, other devices could be employed to cause proximal drive member 49 to rotate with shank 45. For example, shank 45 and the passage in drive member 49 could be polygonal.

Base 43 of tool 41 may comprise a handle for gripping by a user. Optionally, base 43 may have a polygonal drive head 55 formed on its proximal end. In this embodiment, a conventional torque meter or measuring device 57 (FIG. 6) mounts to drive head 55. Torque meter 57 will provide an indication of torque being transmitted by tool 41. A handle 59 is shown connected to the opposite end of torque meter 57 as shown in FIG. 6, for manually rotating tool 41. Torque meter 57 is optional, and if desired, handle 59 could be coupled directly to drive head 55.

As shown in FIG. 8, a series of indicia 61 is preferably formed on shank 45. Indicia 61 comprises numbers or symbols calibrated to provide an indication to the user of the amount of deflection or compression of screw 11 during deployment. The alignment of the proximal side of screw head 17 with a particular number or symbol of indicia 61 informs the operator of the amount of elongation of spring section 25 that has occurred.

Figure 2:
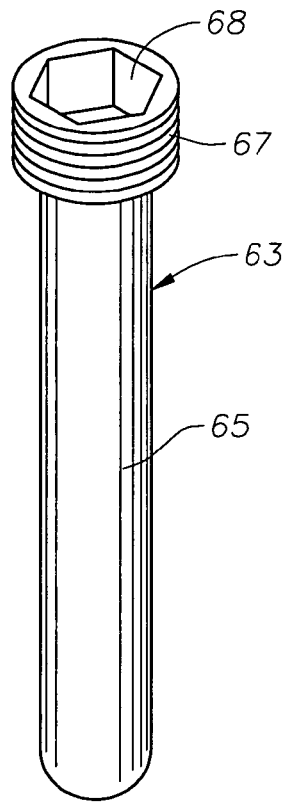
FIG. 2 is a perspective view of a stabilizing pin for insertion into the cavity of the screw after deployment.

Referring to FIG. 2, a stabilizing pin 63 is optionally installed within cavity portion 21a after removal of tool 41. Stabilizing pin 63 has an elongated cylindrical shank 65 and a threaded head 67. Head 67 secures to internal threads 31 in screw 11 (FIG. 1). Head has a drive surface, preferably a socket 68 with drive flanks for receiving a tool (not shown) to secure head 67 to threads 31. The tip of shank 65 locates at the junction between cavity portion 21a and distal drive socket 27. The outer diameter of shank 65 is slightly less than the inner diameter of cavity portion 21a. Stabilizing pin 63 stiffens the construction to prevent bending of spring 25 and possible failure. Also, stabilizing pin 63 serves to retard the ingrowth of bone through helical slot 23 into cavity 21a. Rather than threads 67 engaging internally threaded section 31, other types of retaining mechanisms could be employed, such as a snap ring or retainer ring.

The primary use for the preferred embodiment of screw 11 is as a bone fastener, but it may have other uses as well. FIG. 8 illustrates an example of the primary use of the preferred embodiment. A bone 69 of a patient is shown having a fracture 71, resulting in separate objects or fragments 69a and 69b. To repair fracture 71, the operator or surgeon will first insert a guide pin (not shown), or drill a pilot hole, from fragment 69a into fragment 69b in a conventional manner to provide an accurate axis of insertion of the device. The guide pin is a small diameter elongated member that has a threaded end that secures in the base of the pilot hole. The operator then passes a reamer (not shown) over the guide pin to drill out a hole 73 in fragments 69a and 69b. The diameter of hole 73 is less than the diameter of screw threaded section 15 at the distal end, but the same or slightly larger than the diameter of screw body 13 between threaded section 15 and head 17. The operator selects the depth of hole 73 to be longer than the length of screw 11 by an amount to accommodate the desired elongation of spring section 25. The operator then inserts a tool (not shown) with a threaded tap over the guide wire and into hole 73. The operator rotates the tool to form a set of helical grooves in hole 73 that match the pitch of threads 15. The operator removes the tap, but may leave the guide wire in place, if desired.

The operator slides washer 33 over screw body 13 and places its distal side 37 in contact with bone 69. Distal side 37 is preferably contoured to fit generally flush against the exterior portion of bone 69 surrounding the entrance of hole 73. This exterior portion may be generally convex, as shown, or other shapes. The operator inserts screw 11 over the guide wire, if it is still in place, and into hole 73. Washer 33 will be in contact with the exterior surface of bone 69.

The operator engages tool distal drive member 47 with distal drive socket 27. Simultaneously, the operator pushes proximal drive member 49 axially along tool shank 45 until it fits within proximal drive socket 29. The operator optionally attaches torque meter 57 (FIG. 6) and begins rotation of tool 41. If remaining, the guide wire may extend through a passage provided in tool 41 and torque meter 57. The rotational force is exerted simultaneously against both drive sockets 27, 29. This rotation causes external threads 15 to advance into the threaded profile of hole 73. Because tool 41 drives both drive sockets 27, 29 simultaneously, no torque is applied to spring section 25.

As the operator continues rotating, screw flange 19 will engage washer 33. The spherical surfaces 19 and 35 allow washer 33 to be angularly misaligned up to a selected amount relative to head 17 due to irregular surfaces of bone 69. That is, the axis of washer 33 may be at an acute angle relative to the axis of screw 11. Also, the smooth spherical surfaces 19 and 35 reduce friction due to the rotation of screw 11 that would otherwise occur if head 17 directly contacted the exterior of bone 69. Eventually, the contact of screw head 17 against washer 33 will cause washer 33 to bear tightly against the exterior surface of bone 69, preventing head 17 from any advancing further toward bone 69. Threaded section 15, however, continues to advance into hole 73, causing the overall length of screw 11 to elongate. The elongation takes place in spring section 25. The resiliency of spring section 25 creates a preload force against the exterior side of bone 69. The operator will continue rotating screw 11 until one of the indicia 61 indicates that the desired elongation of screw 11 has taken place. The maximum elongation, typically about 3–6 millimeters, will be precalculated to avoid the torque creating permanent axial deformation of spring section 25. Spring section 25 will thus remain elastic if not elongated past the maximum limit. As a safety backup, the operator may monitor torque meter 57. The amount of compressive load will be proportional to the elongation of screw 11.

Once the desired preload compression has been achieved, the operator will remove tool 41 and the guide wire if it is still in place, then installs stabilizing pin 63. The operator inserts a tool into socket 68 (FIG. 2) in head 67 and tightens stabilizing pin 63 within internally threaded section 31, as shown in FIG. 8. After stabilizing pin 63 has been tightened, the operator removes the tool. Optionally, the operator may coat the exterior of stabilizing pin 63 with bone wax to further retard ingrowth of bone into screw 11 and allow potential contraction of spring section 25. Optionally, the operator could omit stabilizing pin 63 to fill cavity 21 with bone wax or other material to retard ingrowth of bone into cavity 21 and facilitate later removal.

If screw 11 must later be removed, the process is reversed. The operator inserts a tool into socket 68 (FIG. 2) of stabilizing pin 63 and removes stabilizing pin 63. The operator then engages tool 41 with screw 11, having engaged drive member 47 with drive socket 27 and drive member 49 with drive socket 29, and rotates tool 41 in reverse. The back cut flutes 20 (FIG. 5) recut threads in bone 69 when tool 41 is rotated in reverse.

The invention has significant advantages. The spring section applies a continuous compressive force to two objects, such as fragments of bone. The two separate drive surfaces on the opposite ends of the spring section avoid applying torque to the spring section during insertion or removal, which would increase stress and possibly damage the spring section. Allowing the proximal drive member to move axially on the shank of the driving tool allows the distal drive member to remain in engagement with the distal drive socket while the screw elongates. The washer reduces rotary friction and allows compliance of the screw head so that the screw does not have to be precisely normal to the bone surface. The stabilizing pin prevents cyclic bending to protect the deployed spring section when used as a single device. Also, the stabilizing pin retards ingrowth into the screw, which otherwise would make removal move difficult.

While the invention has been shown in only one of its forms, it should be apparent to those skilled in the art that it is not so limited but it is susceptible to various changes without departing from the scope of the invention. For example, although shown for attaching fragments of a bone, the device and tool could be used for fastening any objects that desire a compressive force to remain under dynamic conditions, including industrial applications.

I claim:

1. An apparatus for fastening objects, comprising:
an elongated body having a distal end and a proximal end;
an external anchor section on a distal portion of the body for anchoring the distal portion of the body to an object;
a spring section in the body at a location between the anchor section and the proximal end, the spring section allowing the body to elongate from an initial length when being fastened in the object, but urging the body toward the initial length;
a proximal drive surface at a location proximal of the spring section for imparting torque to the body proximal of the spring section;
a distal drive surface at a location distal of the spring section for imparting torque to the body distal of the spring section at the same time torque is imparted by the proximal drive surface; wherein the body is hollow, and the apparatus further comprises:
a stabilizing pin that is inserted into the body after the body is in full engagement with the object, the stabilizing pin extending through the spring section and being rotatable relative to the spring section during insertion of the stabilizing pin into the body.

2. An apparatus for fastening objects, comprising:
an elongated body having a distal end and a proximal end;
an external anchor section on a distal portion of the body for anchoring the distal portion of the body to an object;
a spring section in the body at a location between the anchor section and the proximal end, the spring section allowing the body to elongate from an initial length when being fastened in the object, but urging the body toward the initial length;
a proximal drive surface at a location proximal of the spring section for imparting torque to the body proximal of the spring section;
a distal drive surface at a location distal of the spring section for imparting torque to the body distal of the spring section at the same time torque is imparted by the proximal drive surface; and
a driving tool having a distal drive member that engages the distal drive surface and a proximal drive member that simultaneously engages the proximal drive surface, the proximal drive member being carried by the driving tool for rotation in unison with the distal drive member.

3. The apparatus according to claim 2, further comprising:
a partially spherical annular flange on the proximal end of the body; and
a washer adapted to contact the object, the washer having an interior shoulder that is partially spherical for mating engagement with the flange.

4. The apparatus according to claim 2, wherein the proximal and distal drive surfaces comprise a plurality of circumferentially spaced drive flanks.

5. The apparatus according to claim 2, wherein the body is hollow and the spring section comprises a helical rib.

6. The apparatus according to claim 2, wherein the body is hollow, and the proximal and distal drive surfaces comprise polygonal drive sockets formed within the body.

7. The apparatus according to claim 2, wherein:
the driving tool has an elongated shank;
the distal drive member is located on the shank; and
the proximal drive member is located on the shank and is axially movable relative to an axis of the shank.

8. An apparatus for fastening objects, comprising:
an elongated body having a distal end and a proximal end;
an external threaded section on a distal portion of the body;
a head formed on the proximal end of the body;
a cavity extending through the head into the body, defining a side wall with an interior side and an exterior side;
a slot extending through the side wall from the interior side to the exterior side, the slot extending helically along the body at a location between the threaded section and the head, defining a spring section;
a proximal drive surface on the body at a location proximal of the spring section to impart torque to the body proximal of the spring section;
a distal drive surface within the cavity at a location distal of the spring section to impart torque to the body distal of the spring section, the proximal and distal drive surfaces being positioned for receiving a tool that simultaneously applies torque to both of the drive surfaces to rotate the threaded section into engagement with an object without applying torque to the spring section; and
a stabilizing pin placed in the cavity after the apparatus has been driven fully into engagement with the object, the stabilizing pin extending through the spring section and being rotatable relative to the body during insertion of the stabilizing pin into the cavity.

9. The apparatus according to claim 8, further comprising:
an internal threaded section in the cavity at a location proximal of the spring section; and
the stabilizing pin has an external threaded section that engages the internal threaded section in the cavity, the stabilizing pin having an elongated shank that extends past the spring section.

10. The apparatus according to claim 8, wherein the proximal drive surface comprises a polygonal socket formed within the head.

11. The apparatus according to claim 8, wherein the cavity extends completely through the body from the distal end to the proximal end.

12. The apparatus according to claim 8, wherein the head has an annular flange that is a portion of a sphere; and wherein the apparatus further comprises:
a washer adapted to contact the object, the washer having an interior profile that is a portion of a sphere for mating engagement with the flange of the head.

13. An apparatus for fastening objects, comprising:
an elongated body having a distal end and a proximal end;
an external threaded section on a distal portion of the body;
a head formed on the proximal end of the body and having an external flange;
a cavity extending through the head into the body, defining a side wall with an interior side and an exterior side;
a slot extending through the side wall from the interior side to the exterior side, the slot extending helically along the body at a location between the threaded section and the head, defining a spring section that elongates when the apparatus is deployed;
a proximal drive socket located within the head;
a distal drive socket located within the cavity distal of the spring section;
a driving tool having an elongated shank that inserts into the cavity to secure the fastener to an object;
a distal drive member located on a distal end of the shank, the distal drive member engaging the distal drive socket to rotate the distal drive socket; and
a proximal drive member carried by the shank for axial sliding movement relative to an axis of the shank for simultaneously engaging the proximal drive socket while the distal drive member engages the distal drive socket and the spring section elongates, the proximal drive member being rotatable with the shank to rotate the proximal drive socket simultaneously with the distal drive socket.

14. The apparatus according to claim 13, further comprising:
an internal threaded section in the cavity at a location proximal of the spring section; and
a stabilizing pin that is positioned in the cavity after the driving tool has been removed, the stabilizing pin having an external threaded section that engages the internal threaded section in the cavity, the stabilizing pin having an elongated shank that extends past the spring section.

15. The apparatus according to claim 13, wherein the flange has a spherical portion; and wherein the apparatus further comprises:
a washer adapted to contact the object, the washer having an interior profile that has a spherical portion for mating engagement with the flange of the head.

16. The apparatus according to claim 13, further comprising a set of indicia on the shank adjacent the proximal drive member for providing an indication of elongation of the spring section.

17. A method of fastening a first object to a second object, comprising:
(a) forming a hole through the first object and into the second object;
(b) providing a fastener with an external anchor section, a spring section, a proximal drive surface at a location proximal of the spring section, and a distal drive surface at a location distal of the spring section;
(c) providing a tool with a distal drive member and a proximal drive member; and
(d) engaging the distal drive member with the distal drive surface and the proximal drive member with the proximal drive surface, inserting the fastener into the hole, and simultaneously rotating the distal and proximal drive members to secure the anchor section in a portion of the hole in the second object; and
after step (d), withdrawing the tool and securing a stabilizing pin within the cavity by rotating the stabilizing pin relative to the fastener.

18. The method according to claim 17, wherein:
step (b) comprises providing the proximal and distal drive surfaces within a cavity of the fastener; and
step (d) comprises inserting the distal and proximal drive members into the cavity.

* * * * *